(12) United States Patent
Velde

(10) Patent No.: US 7,968,769 B2
(45) Date of Patent: Jun. 28, 2011

(54) ALFALFA VARIETY NAMED MAGNUM VI

(75) Inventor: Michael John Velde, Clinton, WI (US)

(73) Assignee: Dairyland Seed Co., Inc., West Bend, WI (US)

( * ) Notice: Subject to any disclaimer, the term of this patent is extended or adjusted under 35 U.S.C. 154(b) by 991 days.

(21) Appl. No.: 11/736,651

(22) Filed: Apr. 18, 2007

(65) Prior Publication Data

US 2008/0263723 A1    Oct. 23, 2008

(51) Int. Cl.
*A01H 5/00* (2006.01)
*A01H 4/00* (2006.01)
*C12N 5/04* (2006.01)

(52) U.S. Cl. ......... 800/298; 800/260; 800/295; 435/410
(58) Field of Classification Search .................. None
See application file for complete search history.

(56) References Cited

U.S. PATENT DOCUMENTS

2005/0204434 A1*   9/2005   Velde .............................. 800/298

OTHER PUBLICATIONS

Hay and Forage, Mar. 1, 2003 (http://hayandforage.com/mag/farming_product_review_7).*

* cited by examiner

*Primary Examiner* — Vinod Kumar
(74) *Attorney, Agent, or Firm* — Michael Best & Friedrich LLP

(57) ABSTRACT

Disclosed is an alfalfa seed designated Magnum VI and deposited as ATCC Accession Number PTA-8324. Also disclosed are plants, or parts thereof, grown from the seed of the cultivar, plants having the morphological and physiological characteristics of the Magnum VI cultivar, and methods of using the plant or parts thereof in an alfalfa breeding program.

18 Claims, No Drawings

ALFALFA VARIETY NAMED MAGNUM VI

CROSS REFERENCE TO RELATED APPLICATIONS

Not applicable.

BACKGROUND OF THE INVENTION

Alfalfa (*Medicago sativa*) has often been referred to as the "Queen of Forages" because it is an excellent source of protein and digestible fiber, and because of its wide adaptation. Alfalfa has a high mineral content and contains at least 10 different vitamins and is an important source of vitamin A. Alfalfa improves soil tilth, and, in symbiosis with nitrogen fixing bacteria, is highly effective in converting atmospheric nitrogen to biological nitrogen. Thus, alfalfa is an ideal crop for use in crop rotation to improve soil tilth and replenish nutrients depleted from the soil by other crops such as corn.

The environment in which plants are grown for agricultural production continuously offers new obstacles to agricultural production, including, for example, changes in weather conditions, pests, and disease. Plant science agriculture involves manipulation of available plant resources to meet the needs of the growing human and animal populations. Each new cultivar or variety released to agricultural production is selected for the purpose of increasing yield resulting from increased disease resistance to prevalent diseases, or from direct or indirect improvement in yield potential or efficiency of production. Development of stable, high yielding cultivars with superior characteristics is an ongoing goal of alfalfa breeders.

Thus, there is a need in the art for a novel alfalfa cultivars and alfalfa seed.

BRIEF SUMMARY OF THE INVENTION

In one aspect, the present invention provides a Medicago sativa seed or cultivated alfalfa seed designated Magnum VI and deposited under the terms of the Budapest Treaty and in accordance with 37 C.F.R. §§ 1.801-1.809 on Apr. 10, 2007 with the American Type Culture Collection (ATCC), Manassas, VA, under Accession Number PTA-8324.

In another aspect, the present invention includes a Medicago sativa alfalfa plant or cultivated alfalfa plant derived from the seed designated Magnum VI and deposited under Accession Number PTA-8324. The plant may be grown directly from the seed deposited under Accession Number PTA-8324, or may be obtained indirectly from a plant grown directly from the seed by any suitable methods. For example, the plant may be generated from seed produced by a plant grown directly from the seed, from a cutting taken from a plant grown directly from the seed, or from tissue culture or callous derived from cells from a plant grown directly from the seed. The invention includes succeeding generations of plants derived from plants grown from the seed of Accession Number PTA-8324.

In another aspect, the present invention provides tissue culture of regenerable cells from a plant, or parts thereof, produced by growing seed deposited under Accession Number PTA-8324 and designated Magnum VI and alfalfa plants regenerated from the tissue culture In other aspects, the present invention includes the pollen and ovule of a plant derived from the seed deposited under Accession Number PTA-8324.

The present invention also provides a method for developing an alfalfa plant in an alfalfa breeding program using plant breeding techniques, comprising using an alfalfa plant, or part thereof, produced by growing seed designated Magnum VI as a source of breeding material.

Other features and advantages of the invention will be apparent upon review of the specification.

BRIEF DESCRIPTION OF THE SEVERAL VIEWS OF THE DRAWINGS

Not applicable.

DEFINITIONS

Terms used in the descriptions and tables that follow are defined as follows:

Flower color: Modern alfalfas are characterized by flower colors: purple, variegated, white, yellow and cream. Some cultivars are heterogeneous for flower color whereby some are predominately purple and variegated.

Forage yield is measured by harvesting herbage for part of or the entire life of the stand.

Fall dormancy: Alfalfa is classified into fall dormancy classes numbered 1 through 10, where dormancy group 1 is very dormant suited for cold climates and dormancy group 10 is very non-dormant and suited for very hot climates in which the plant would grow through out the winter months.

Winter survival: This evaluation is a prediction of the ability of the plant to persist over time.

Persistence: The ability of the cultivar to last over a minimum of two years. This measurement is documented in the visual percent stand remaining at the time of observation.

Anthracnose: Anthracnose is a serious stem and crown rot disease of alfalfa which can kill individual plants and cause rapid stand decline. Anthracnose is caused by *Colletotrichum trifolii*, a fungus which produces masses of tiny spores on infected stems and crowns. During periods of hot, rainy weather, spores are splashed from infected to healthy plants. Lesions develop on stems, causing stems to wilt and eventually die. The pathogen grows from stem tissue into the plant crown, and causes a crown rot which ultimately kills the plant.

*Aphanomyces* Root Rot: *Aphanomyces* root rot is caused by the fungal-like pathogen *Aphanomyces* euteiches causes death and poor growth of seedling alfalfa in slowly drained fields. It also can be a chronic disease of established plants that may result in significant yield reduction. *Aphanomyces* root rot is similar to and may occur in a complex with *Phytophthora* root rot and *Pythium* damping off, diseases which also occur in wet or slowly drained soils. Plants infected with *Aphanomyces* usually are stunted and chlorotic before they wilt and die, whereas *Phytophthora* and *Pythium* tend to kill seedlings quickly before plants become severely chlorotic.

Bacterial Wilt: The disease is caused by *Clavibacter michiganense* subsp. *insidiosum* (McCulloch) Davis et. al.=*Corynebacterium insidiosum* (McCulloch) Jensen. The bacterium survives in plant material in the soil, hay and seed for several years. It can be spread plant to plant via surface water (rain) irrigation and contaminated implement. Bacterial wilt is most common on plants growing in low, poorly drained areas of the field. It is also more common in wet years. Primary infection occurs when bacteria enter roots via wounds. Wounding can be caused by insect or nematode feeding, winter injury of mechanical injury. Once the bacterium enters the plant, symptoms are slow to develop, usually visible in the second or third crop year.

*Fusarium* Wilt: This disease is caused by *Fusarium oxysporum* f. sp. *Medicagines*. Wilting shoots are the first evidence of the disease. In early stages, the leaves may wilt during the day and regain turgidity at night. Bleaching of the leaves and stems follows, and a reddish tinge often develops in the leaves. Only one side of a plant may be affected at first, and after several months, the entire plant dies. Dark or reddish brown streaks occur in the roots appearing in cross section as small partial or complete rings.

*Phytophthora* Root Rot: *Phytophthora* root rot is caused by a soil-borne fungus, *Phytophthora medicaginis*, which is present in most alfalfa field soils. This fungus survives in organic debris and becomes active in wet soil. Water-saturated soils allow production of zoospores which have the capability to "swim" to roots and begin the infection process. Infection usually occurs on small lateral roots. From these initial infection points, the fungus gradually grows into the taproot. A yellow, red, or purple discoloration of leaves is the most characteristic above-ground symptom of *Phytophthora* root rot. Damage is most evident in low or poorly-drained areas of a field.

*Verticillium* Wilt: *Verticillium* wilt is caused by a fungus, *Verticillium albo-atrum*, which enters the water-conducting cells of the alfalfa plant and restricts the upward movement of water and nutrients. The fungus produces spores within the plant, or on cut stem surfaces following harvesting operations. Spores germinate on the cut surfaces and produce filaments (hyphae) that grow into stems and ultimately into roots. *Verticillium* wilt symptoms usually do not become conspicuous until the third production year. A yellow, V-shaped discoloration at the tip of a leaflet is an early indication of *Verticillium* infection. Eventually, leaflets wilt, turn yellow or pink, and often curl or twist. These abnormally small, twisted leaflets occurring near the top of the stem are the most characteristic symptoms of the disease. Stems are stunted, but frequently remain green and erect (in contrast to the drooping stems caused by anthracnose). Taproots appear healthy and sound, but have a dark ring (the water-conducting tissues) which is evident when the taproot is cut in cross section.

Pea Aphid: The long-legged pea aphid *Acyrthosiphon pisum* (Harris) adult is light to deep green with reddish eyes. It has a body length of 2.0 to 4.0 mm and most adults are wingless. The cornicles (a pair of tailpipe-like structures projecting from the abdomen) of this aphid are characteristically long and slender. The egg is approximately 0.85 mm long; the light green egg turns a shiny black before hatching. The nymph, the immature aphid is smaller than, but similar to, the larger wingless adult. It requires four molts to reach the adult stage. Pea aphids extract sap from the terminal leaves and stem of the host plant. Their feeding can result in deformation, wilting, or death of the host depending upon the infestation level. Plants that survive heavy infestations are short and bunchy with more lightly colored tops than those of healthy plants. Wilted plants appear as brownish spots in the field. Moreover, plants are often coated with shiny honeydew secreted by the aphids, and cast skins may give the leaves and ground a whitish appearance.

DETAILED DESCRIPTION OF THE INVENTION

In one aspect, the present invention includes the seed of alfalfa cultivar Magnum VI deposited under the Budapest Treaty and in accordance with 37 C.F.R. §§ 1.801-1.809 on Apr. 2, 2007 with the American Type Culture Collection in Manassas, VA as Accession Number PTA-8324, and plants or plant parts derived from the seed deposited as Accession Number PTA-8324.

By "a plant derived from the seed deposited as Accession Number PTA-8324", it is meant a plant that is grown directly from the seed deposited as Accession Number PTA-8324, or a plant that is obtained indirectly from a plant grown from the seed deposited as Accession Number PTA-8324. Plants obtained indirectly from a plant grown from the seed deposited as Accession Number PTA-8324 may be grown from a vegetative cutting, seed, callus or tissue culture obtained from a plant or plant part grown from the seed deposited as Accession Number PTA-8324 or a clonal plant thereof.

Magnum VI has superior characteristics and is a 121 clone synthetic. Parent clones were selected out of forage yield plots and/or disease nurseries. The parent plants were progeny tested for one or more of the following traits: forage yield, stand persistence, forage quality, resistance of bacterial wilt, *Fusarium* wilt, *Phytophthora* root rot, anthracnose (Race 1), *Verticillium* wilt and *Aphanomyces* root rot (Race 1). All of the parent plants trace back to Dairyland experimental plants. Parent plants were planted in field isolation and inter-pollinated by honey (*Apis mellifera*), leaf cutting (*Megachili rotundata*) and bumble bees (*Bombus impatiens*) near Sloughhouse, Calif. in 2001 to produce Syn. 1 as Breeder seed. Seed from parent plants were equally bulked each year to produce Breeder seed.

Breeder seed (Syn. 1) was produced by bulking seed of parent plants which were grown in field isolation near Sloughhouse, Calif. in 2001. Seed from parental clones were equally bulked. Foundation seed (Syn. 2) was produced from Breeder seed and Certified seed (Syn. 2 or 3) from either Breeder or Foundation seed. One generation each of Breeder, Foundation and two generations of Certified seed classes are recognized. A maximum of three harvest years each is permitted on stands producing Breeder and Foundation seed. A maximum of five harvest years is permitted for Certified seed. Dairyland Research International will maintain sufficient Breeder seed for the projected life of the variety.

The present invention contemplates using the Magnum VI plant, or part thereof, or an alfalfa plant having the physiological and morphological characteristics of the Magnum VI plant, as a source of hay, haylage, greenchop and dehydration.

Magnum VI was found to be highly resistant to: anthracnose (*Colletotrichum trifolii*), *Aphanomyces* root rot (Race 1) (*Aphanomyces euteiches*), bacterial wilt (*Clavibacter michiganense*), *Fusarium* wilt (*Fusarium oxysporum*), *Phytophtora* root rot (*Phytophthora megasperma*), *Verticillium* wilt (*Verticillium albo-atrum*) and moderate resistance to pea aphid (*Acyrthosipon pisum*).

Magnum VI is a moderately dormant variety similar to the fall dormancy 4 check. It expresses 7 and 41% better persistence than 5312 and Vernal respectively. Magnum VI winter survival is similar to that of the very winter hardy check. Flower color in the Syn. 2 generation is 90% purple, 10% variegated with trace amounts of cream, white and yellow. Magnum VI forage yield performance expresses a 7% advantage over 21 popular conventional varieties across 390 harvests. Its forage yield performance is 10% better than five popular ROUNDUP herbicide tolerant alfalfa varieties across 36 harvests.

The present invention contemplates using the Magnum VI alfalfa plant, or part thereof, or an alfalfa plant having the physiological and morphological characteristics of the Magnum VI alfalfa plant, as a source of breeding material for developing or producing an alfalfa plant in an alfalfa breeding program using plant breeding techniques. Plant breeding techniques useful in the developing or producing alfalfa plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature.

As used herein, the term "plant" includes, but is not limited to, plant cells, plant protoplasts, plant cell tissue cultures from which alfalfa plants can be regenerated, plant calli, plant clumps, and plant cells that are intact in plants or parts thereof. "Plant part" includes, but is not limited to, embryos, pollen (pollen grains), ovules, seeds, flowers, pods, leaves, roots, root tips, anthers, and the like.

One may obtain alfalfa plants according to the present invention by directly by growing the seed Magnum VI or by any other means. An alfalfa plant having all of the physiological and morphological characteristics of Magnum VI can be obtained by any suitable methods, including, but not limited to, regenerating plants or plant parts from tissue culture or cuttings. The scope of the present invention is not limited by the method by which the plant is obtained.

The following non-limiting examples are intended to be purely illustrative.

EXAMPLES

Disease Resistance of Cultivar and Cultivar Components

The response of Magnum VI to various diseases was evaluated according to the "Standard Tests to Characterize Alfalfa Cultivars, $3^{rd}$ edition, as amended July 1998", approved by the North American Alfalfa Improvement Conference. The resistance or susceptibility of the cultivar to anthracnose (*Colletotrichum trifolii*), Aphanomyces root rot (Race 1), (*Aphanomyces euteiches*), bacterial wilt (*Clavibacter michiganense*), Fusarium wilt (*Fusarium oxysporum*), Phytophthora root rot (*Phytophthora megasperma*), Verticillium wilt (*Verticillium albo-atrum*), and pea aphid (*Acyrthosipon pisum*) were assessed. For each disease tested, appropriate check cultivars, including resistant and susceptible cultivars, were employed as controls. The results are presented in Tables 1 through 7.

For each type of disease tested, each line of plants was assigned to one of five classes of resistance according to the percentage of resistant plants as follows:

| Class | % Resistant plants |
| --- | --- |
| Susceptible | <6 |
| Low resistant | 6-14 |
| Moderately resistant | 15-30 |
| Resistant | 31-50 |
| Highly resistant | >50 |

Fall Dormancy

Magnum VI is a moderately dormant variety similar to the fall dormancy 4 ("FD4") check. See Tables 8A and 8B.

Persistence Advantage of Magnum VI

Persistence of Magnum VI showed a 7% advantage over check variety 5312 and a 41% advantage over check variety Vernal. See Table 9.

Survival of Over Wintered Plants

Magnum VI winter survival is similar to the very hardy winter check. See Tables 10A and 10B.

Flower Color

Magnum VI flower color was classified according to the USDA Agriculture Handbook No. 424-A System for Visually Classifying Alfalfa Flower Color. Flower color in the Syn. 2 generation is 90% purple, 10% variegated with trace amounts of cream, white and yellow. See Table 11.

Forage Yield

Forage yields of Magnum VI were measured and are presented on Tables 12 and 13. Magnum VI showed a forage yield performance expressing a 7% advantage over 21 popular conventional varieties across 390 harvests. See Table 12. Magnum VI showed yield performance that is 10% better than five popular ROUNDUP READY herbicide tolerant alfalfa varieties across 36 harvests. See Table 13.

TABLE 1

Resistance to anthracnose (Race 1) disease (*Colletotrichum trifolii*)
Test conducted by Dairyland Research at Clinton, WI.

| Variety | Resistance Class | Year Tested | Syn Gen | Unadjusted % R | Adjusted % R |
| --- | --- | --- | --- | --- | --- |
| Magnum VI | HR | 2005 | 1 | 65 | 64 |
| 1. Saranac AR | R | | | 46 | 45 |
| 2. Saranac | S | | | 2 | 2 |
| Test Mean: | | | | 54 | 53 |
| L.S.D. (.05%) | | | | 12 | |
| C.V. (%) | | | | 10 | |

Note:
Unadjusted % R is the actual raw data summary.
Adjusted % R is transformed to the standards of the resistant check.

TABLE 2

Resistance to *Aphanomyces* Root Rot (Race 1) (*Aphanomyces euteiches*)
Test conducted by Dairyland Research at Clinton, WI.

| Variety | Resistance Class | Year Tested | Syn Gen | Unadjusted % R | Adjusted % R |
|---|---|---|---|---|---|
| Magnum VI | HR | 2005 | 1 | 65 | 59 |
| 1. WAPH-1 | HR | | | 55 | 50 |
| 2. Saranac | S | | | 1 | 1 |
| Test Mean: | | | | 45 | 41 |
| L.S.D. (.05%) | | | | 10 | |
| C.V. (%) | | | | 12 | |

TABLE 3

Resistance to Bacterial Wilt Disease (*Clavibacter michiganense*)
Test conducted by Dairyland Research at Clinton, WI.

| Variety | Resistance Class | Year Tested | Syn Gen | Unadjusted % R | Adjusted % R |
|---|---|---|---|---|---|
| Magnum VI | HR | 2006 | 2 | 84 | 71 |
| 1. Vernal | R | | | 50 | 42 |
| 2. Narragansett | S | | | 4 | 3 |
| Test Mean: | | | | 71 | 60 |
| L.S.D. (.05%) | | | | 7 | |
| C.V. (%) | | | | 12 | |

TABLE 4

Resistance to *Fusarium* Wilt Disease (*Fusarium oxysporum*)
Test conducted by Dairyland Research at Clinton, WI.

| Variety | Resistance Class | Year Tested | Syn Gen | Unadjusted % R | Adjusted % R |
|---|---|---|---|---|---|
| Magnum VI | HR | 2006 | 2 | 69 | 70 |
| 1. Agate | HR | | | 53 | 54 |
| 2. MNGN-1 | S | | | 8 | 8 |
| Test Mean: | | | | 72 | 73 |
| L.S.D. (.05%) | | | | 10 | |
| C.V. (%) | | | | 8 | |

TABLE 5

Resistance to *Phytophthora* Root Rot Disease (*Phytophthora medicaginis*)
Test conducted by Dairyland Research at Clinton, WI.

| Variety | Resistance Class | Year Tested | Syn Gen | Unadjusted % R | Adjusted % R |
|---|---|---|---|---|---|
| Magnum VI | HR | 2005 | 1 | 63 | 63 |
| 1. WAPH-1 | HR | | | 55 | 55 |
| 2. Saranac | S | | | 4 | 4 |
| Test Mean: | | | | 42 | 42 |
| L.S.D. (.05%) | | | | 9 | |
| C.V. (%) | | | | 13 | |

TABLE 6

Resistance to *Verticillium* Wilt Disease (*Verticillium albo-atrum*)
Test conducted by Dairyland Research at Clinton, WI.

| Variety | Resistance Class | Year Tested | Syn Gen | Unadjusted % R | Adjusted % R |
|---|---|---|---|---|---|
| Magnum VI | HR | 2004 | 1 | 56 | 62 |
| 1. Vertus | R | | | 36 | 40 |
| 2. Saranac | S | | | 1 | 1 |
| Test Mean: | | | | 42 | 47 |
| L.S.D. (.05%) | | | | 13 | |
| C.V. (%) | | | | 16 | |

TABLE 7

Resistance to Pea Aphid Insect (*Acyrthosipon pisum*)
Test conducted by Dairyland Research at Clinton, WI.

| Variety | Resistance Class | Year Tested | Syn Gen | Unadjusted % R | Adjusted % R |
|---|---|---|---|---|---|
| Magnum VI | MR | 2005 | 1 | 23 | 24 |
| 1. CUF 101 | HR | | | 53 | 55 |
| 2. Ranger | S | | | 7 | 7 |
| Test Mean: | | | | 31 | 32 |
| L.S.D. (.05%) | | | | 9 | |
| C.V. (%) | | | | 19 | |

TABLE 8A

Fall Dormancy
Fall dormancy as determined from spaced plantings relative
to three (3) standard check varieties.
Test conducted by Dairyland Research at Clinton, WI.

| Test Location | Syn Gen | Date Last Cut (Mo/Yr) | Date Measured (Mo/Yr) | This Variety | 1. 5246 (FD3) | 2. Legend (FD4) | 3. Archer (FD5) | LSD .05 | CV % |
|---|---|---|---|---|---|---|---|---|---|
| Clinton, WI | F1 | 9/05 | 10/05 | 12 | 9 | 12 | 15 | 2.1 | 16 |

Scoring system used: Fall growth in inches

TABLE 8B

Fall Dormancy
Indicate which of the following fall dormancy classes this variety is most similar to.

| Very Dormant | Dormant | Moderately Dormant | Non-Dormant | Very Non-Dormant |
|---|---|---|---|---|
| FD 1 ( ) | FD 2 ( ) | FD 4 (X) | FD 7 ( ) | FD 9 ( ) |
|  | FD 3 ( ) | FD 5 ( ) | FD 8 ( ) |  |
|  |  | FD 6 ( ) |  |  |

TABLE 11

Flower Color
Flower color at full bloom. Syn. 2 generation observed.
(See USDA Agriculture Handbook No. 424—A System for Visually Classifying Alfalfa Flower Color.)

| Color | Percent |
|---|---|
| Purple | 90% |
| Variegated | 10% |
| Cream | Trace |
| Yellow | Trace |
| White | Trace |

TABLE 9

Persistence
Test conducted by Dairyland Research at Potsdam, MN.

| | | | | | % Stand | | | | |
|---|---|---|---|---|---|---|---|---|---|
| | | | | Date of | | Check Varieties | | | |
| | | Date | | Readings | | | | | |
| Test Location | Syn Gen | Seeded Mo/Yr | # of Years Harvester | # of Harvests | (Mo/Yr) Initial/Final | This Variety Initial/Final | Vernal Initial/Final | 5312 Initial/Final | LSD .05 | CV % |
| Postdam, MN | 1 | 5/04 | 3 | 8 | 5/04/5/06 | 100/55 | 100/39 | 100/51 | 17 | 21 |

TABLE 10A

Winter Survival
Winter survival as determined from spaced plantings relative to standard check varieties; check varieties must be chosen so as to bracket the winter survival data of this variety. Data for check varieties in classes 1 through 6 must be included. This claim must be supported by data from a minimum of two (2) independent trial/location years. A single test run at one location for two (2) consecutive years is insufficient.
Tests conducted by Dairyland Research at Clinton, WI.

| | | | | | Winter Survival Rating | | | | | | | |
|---|---|---|---|---|---|---|---|---|---|---|---|---|
| Test Location | Syn Gen | Date Planted (Mo/Yr) | Date Measured (Mo/Yr) | This Variety | 1 | 2 | Check Class 3 | 4 | 5 | 6 | LSD .05 | CV % |
| Clinton, WI | 1 | 4/04 | 5/05 | 2.0 | 1.8 | 2.1 | 2.8 | 3.2 | 4.1 | 5.0 | .45 | 12 |
| Clinton, WI | 2 | 4/05 | 5/06 | 2.2 | 1.5 | 2.3 | 2.7 | 3.8 | 4.3 | 5.0 | .60 | 15 |

TABLE 10B

Winter Survival
Note the check variety used for each class (X). Also indicate the winter survival class to which this variety is most similar {X}.

| 1 { } | 2 {X} | 3 { } | 4 { } | 5 { } | 6 { } |
|---|---|---|---|---|---|
| Extremely Winterhardy | Very Winterhardy | Moderately Winterhardy | Low Winterhardy | Winterhardy | Non-Winterhardy |
| (X) ZG9830 | (X) 5262 | (X) WL32 | (X) G2852 | (X) Archer | (X) CUF 101 |
| ( ) Maverick | ( ) Vernal | ( ) 5Dart | ( ) G2852 | ( ) S. Special | ( ) Moapa 69 |
| ( ) Norseman | ( ) 526 | ( ) Ranger | ( ) WL 316 | ( ) Sutter | ( ) 5929 |

TABLE 12

Magnum VI
Head to Head Forage Yield Summary
Data collected across at various Midwest locations

| Variety | Total Tons | % Advantage | # of Harvests |
|---|---|---|---|
| Magnum VI | 706.4 | 107 | 390 |
| Competitor | 659.18 | | |

| Variety | Total Tons | % Advantage | # of Harvests |
|---|---|---|---|
| Magnum VI | 13.98 | 106 | 8 |
| 53Q30 | 13.17 | | |
| Magnum VI | 44.07 | 109 | 23 |
| 54Q25 | 40.44 | | |
| Magnum VI | 61.72 | 104 | 34 |
| 54V46 | 59.14 | | |
| Magnum VI | 42.33 | 106 | 25 |
| 5312 | 39.79 | | |
| Magnum VI | 40.13 | 109 | 19 |
| 6400HT | 36.82 | | |
| Magnum VI | 50.54 | 105 | 28 |
| 6415 | 48.24 | | |
| Magnum VI | 4.16 | 106 | 3 |
| Ameristand 407TQ | 3.94 | | |
| Magnum VI | 17.41 | 105 | 7 |
| Extreme | 16.59 | | |
| Magnum VI | 8.2 | 109 | 6 |
| GH707 | 7.55 | | |
| Magnum VI | 57.38 | 100 | 31 |
| Genoa | 57.22 | | |
| Magnum VI | 25.61 | 104 | 13 |
| Lightning III | 24.62 | | |
| Magnum VI | 42.33 | 114 | 25 |
| Oneida VR | 37.07 | | |
| Magnum VI | 31.59 | 104 | 15 |
| Phabulous II | 30.4 | | |
| Magnum VI | 7.14 | 115 | 5 |
| Phabulous III | 6.21 | | |
| Magnum VI | 25.61 | 107 | 13 |
| Rebound 5.0 | 23.88 | | |
| Magnum VI | 22.38 | 105 | 14 |
| SummerGold | 21.36 | | |
| Magnum VI | 22.38 | 105 | 14 |
| WL319HQ | 21.36 | | |
| Magnum VI | 26.21 | 113 | 14 |
| WL343HQ | 23.17 | | |
| Magnum VI | 25.61 | 105 | 13 |
| WL348AP | 24.5 | | |
| Magnum VI | 8.2 | 102 | 6 |
| WL357HQ | 8.04 | | |
| Magnum VI | 67.63 | 113 | 38 |
| Vernal | 59.63 | | |

TABLE 13

Magnum VI
ROUNDUP READY Head to Head Forage Yield Summary
Data collected across at various Midwest locations

| Variety | Total Tons | % Advantage | # of Harvests |
|---|---|---|---|
| Magnum VI | 61.78 | 110 | 36 |
| RR Competitor | 56.04 | | |
| Magnum VI | 8.55 | 112 | 6 |
| 4G418RR | 7.66 | | |
| Magnum VI | 10.75 | 109 | 7 |
| 6443RR | 9.82 | | |
| Magnum VI | 12.23 | 115 | 7 |
| DKA34-17RR | 10.62 | | |
| Magnum VI | 19.07 | 109 | 10 |
| DKA41-18RR | 17.56 | | |
| Magnum VI | 11.18 | 108 | 6 |
| WL355RR | 10.38 | | |

As the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed:

1. A Medicago sativa seed designated as Magnum VI, wherein a sample of said seed has been deposited as ATCC Accession Number PTA-8324.

2. A plant, or a part thereof, produced by growing the seed of claim 1.

3. A pollen from the plant of claim 2.

4. An ovule from the plant of claim 2.

5. An alfalfa plant having all the physiological and morphological characteristics of the plant of claim 2.

6. A tissue culture of regenerable cells from the plant, or the part thereof, of claim 2.

7. The tissue culture of regenerable cells of claim 6 selected from the group consisting of protoplasts and calli, and wherein said regenerable cells are from a leaf, pollen, ovule, cotyledon, hypocotyl, embryo, root, pod, flower, shoot or stalk.

8. A protoplast produced from the tissue culture of claim 6.

9. The tissue culture of claim 6, wherein the culture is a callus culture.

10. An alfalfa plant regenerated from the tissue culture of claim 6, wherein the plant has all of the physiological and morphological characteristics of a plant produced by growing a seed designated Magnum VI and deposited under ATCC Accession No. PTA-8324.

11. A tissue culture of regenerable cells from the plant, or the part thereof, of claim 5.

12. The tissue culture of claim 11, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

13. A protoplast produced from the tissue culture of claim 11.

14. The tissue culture of claim 11, wherein the culture is a callus culture.

15. An alfalfa plant regenerated from the tissue culture of claim 11, wherein the plant has all of the physiological and morphological characteristics of a plant produced by growing a seed designated Magnum VI and deposited under ATCC Accession No. PTA-8324.

16. A method for producing an alfalfa cultivar Magnum VI-derived alfalfa plant, comprising:
 (a) crossing the plant of claim 2 which is produced by growing an alfalfa seed deposited as ATCC Accession No. PTA-8324 with a second alfalfa plant to yield progeny alfalfa seed; and
 (b) growing said progeny seed to yield an alfalfa cultivar Magnum VI-derived alfalfa plant.

17. The method of claim 16, further comprising:
 (c) crossing the alfalfa cultivar Magnum VI-derived alfalfa plant of (b) with itself or a third alfalfa plant to yield a second alfalfa Magnum VI-derived alfalfa progeny seed; and
 (d) growing the second alfalfa progeny seed of (c) to yield a second alfalfa cultivar Magnum VI-derived alfalfa plant.

18. The method of claim 17, wherein (c) and (d) are repeated at least one time to generate an additional alfalfa cultivar Magnum VI-derived alfalfa plant.

* * * * *